Figure 1:
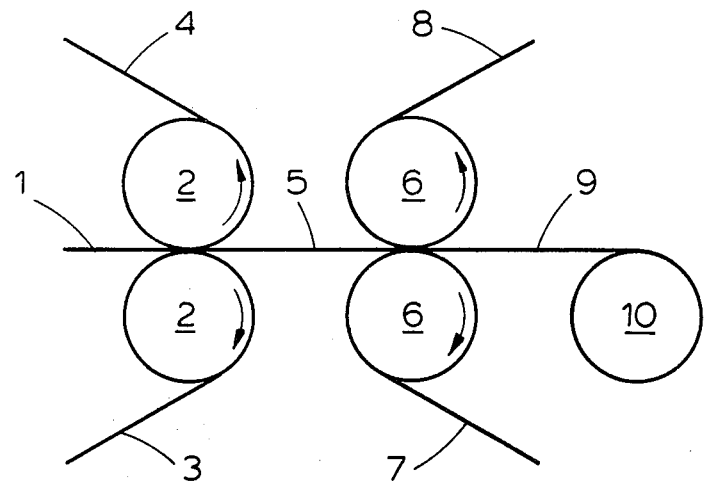

United States Patent [19]
Berry

[11] 4,414,970
[45] Nov. 15, 1983

[54] ELASTIC BANDAGES

[75] Inventor: Peter W. Berry, Bishops Stortford, England

[73] Assignee: Smith and Nephew Associated Companies Limited, United Kingdom

[21] Appl. No.: 286,567

[22] Filed: Jul. 24, 1981

[30] Foreign Application Priority Data

Jul. 30, 1980 [GB] United Kingdom ............... 8024855
Aug. 27, 1980 [GB] United Kingdom ............... 8027719

[51] Int. Cl.³ ............................................. A61L 15/00
[52] U.S. Cl. .................................................. 128/156
[58] Field of Search ............... 128/155, 156, 334 R, 128/169

[56] References Cited

U.S. PATENT DOCUMENTS

| | | | |
|---|---|---|---|
| 3,645,835 | 2/1972 | Hodgson | 128/156 X |
| 3,842,832 | 10/1974 | Wideman et al. | 128/169 |
| 3,888,248 | 6/1975 | Moore et al. | 128/156 |
| 3,896,802 | 7/1975 | Williams | 128/156 |
| 4,060,081 | 11/1977 | Yannas et al. | 128/156 |

FOREIGN PATENT DOCUMENTS

| | | |
|---|---|---|
| 1535322 | 4/1970 | Fed. Rep. of Germany . |
| 482683 | 4/1938 | United Kingdom . |
| 895844 | 5/1962 | United Kingdom . |
| 1041792 | 9/1966 | United Kingdom . |
| 1167345 | 10/1969 | United Kingdom . |
| 1198391 | 7/1970 | United Kingdom . |
| 1367959 | 9/1974 | United Kingdom . |
| 1476894 | 6/1977 | United Kingdom . |
| 1568404 | 5/1980 | United Kingdom . |
| 1571049 | 7/1980 | United Kingdom . |
| 2056910 | 3/1981 | United Kingdom . |
| 1594587 | 7/1981 | United Kingdom . |

Primary Examiner—John D. Yasko
Attorney, Agent, or Firm—Jacobs & Jacobs

[57] ABSTRACT

Moisture vapor transmitting elastic bandages which comprise an inner layer of fabric and an outer layer of fabric bonded to a central layer characterized in that the central layer comprises an elastomeric film are described.

12 Claims, 3 Drawing Figures

ELASTIC BANDAGES

The present invention is concerned with elastic bandages and methods of their manufacture.

Elastic bandages in adhesive and non-adhesive form are used inter alia to provide support and to assist in the healing of strained muscles and in the treatment of various venous conditions where it is important to maintain a level of compressive force for considerable periods of time.

Known elastic bandages have employed crimped yarns, high twist cotton yarns or elastic threads. Elastic woven bandages containing crimped yarns have relatively poor elastic properties. Elastic woven bandages containing high twist cotton yarns which are shrunk during processing are expensive to manufacture and also have relatively poor elastic properties which can be badly affected by moisture. Elastic bandages formed by weaving elastic warp threads under tension into a woven structure have good elastic properties but are expensive to produce and can cause local constriction at the location of individual threads.

British Patent Specification No. 895,844 discloses an air permeable elastic bandage which consists of two outer layers of foam bonded to an intermediate layer of reinforcing fabric. The use of foam layers can avoid the problems of local constriction by providing the bandage with uniform elastic properties over the width of the bandage. However, it is difficult to design and manufacture an elastic bandage with good reproducible elastic compression properties without using foam layers which are comparatively thick in relation to the thickness of the fabric layers. Thick foam layers would also increase the bulk of the elastic bandages.

A class of elastic bandages have now been discovered that have good elastic properties which can be uniform over the width of the bandage. These new bandages also offer the advantage of being relatively easy to manufacture.

The present invention provides a moisture vapour transmitting elastic bandage which comprises an inner layer of fabric and an outer layer of fabric bonded to a central layer characterised in that the central layer comprises an elastomeric film.

The fabric may be woven or non-woven. It is preferred to use non-woven fabrics in the bandages of this invention.

The use of a non-woven fabric in elastic bandages of the invention can provide a desirable textile 'feel' to the surface of the bandage. Additionally use of an absorbent non-woven fabric can provide the bandage with a degree of absorbency for water and body fluids such as blood.

Another preferred fabric is an integral thermoplastic net.

The term 'integral thermoplastic net' means a thermoplastic net formed with junctures integral with the strands of the net, for example thermoplastic nets formed by extrusion or by biaxially stretching an embossed sheet. Such nets are effectively non-elastic.

In this specification the term 'non-woven fabric' does not include integral thermoplastic nets.

The use of an integral thermoplastic net can provide the elastic bandages of the invention with a bandage surface which has abrasion resistance in both dry and moist conditions. Advantageously in adhesive elastic bandages of the invention the net bandage surface can act as an effective adhesive release surface which may allow the adhesive bandage to be easily unrolled without the need to employ expensive interleaving adhesive protectors.

Integral thermoplastic nets can be made in different forms which can provide elastic bandages of this invention with additional advantages hereafter described.

The moisture vapour transmitting elastic bandage of the invention can have a number of alternative constructions. A favoured elastic bandage construction consists of two layers of non-woven fabric bonded to a central layer of an elastomeric continuous film as hereinafter described.

Another favoured elastic bandage construction consists of an outer layer of integral thermoplastic net and an inner layer of absorbent non-woven fabric bonded to a central layer of elastomeric continuous film.

It is desirable that the bandage of this invention should have a sufficient level of moisture vapour transmission to prevent maceration of the skin or a 'clammy feeling' due to the build up of moisture under the bandage. It is therefore desirable that the bandage should have a moisture vapour transmission rate of at least 150 g, more suitably at least 350 g and preferably at least 500 $g/cm^2/24$ hours at 37° C. at 100%-10% relative humidity difference.

The moisture vapour transmission rate may be measured by the Payne Cup method. The method uses a cup 1.5 cm deep with a flanged top. The inner diameter of the flange is such to provide an area for moisture vapour transmission of 10 $cm^2$. In this method 10 ml of distilled water is added to the cup and a sample of the material under test, large enough to completely cover the flange, is clamped over the cup. The complete assembly is then weighed and placed in a cabinet where the temperature and relative humidity are maintained at 37° C. and 10% respectively. After 17 hours the cup is removed from the cabinet and allowed to cool at room temperature. After re-weighing, the mass of water lost by vapour transmission is calculated and the result expressed as in $g/m^2/24$ hr at 37° C., 100%-10% relatively humidity difference.

It follows from the nature of the product that the fabric layers of elastic bandages of the invention will be extensible in the length direction of the bandage. Preferred extensible fabric layers are in a compressed state in the length direction.

Another aspect of this invention provides a moisture vapour transmitting elastic bandage of the invention in which a layer of fabric is in a compressed state in the length direction.

Another desirable aspect of this invention provides a moisture vapour transmitting elastic bandage in which a layer of non-woven fabric is in a compressed state in the length direction.

A particularly desirable aspect of this invention provides a moisture vapour transmitting elastic bandage in which a layer of integral thermoplastic net is in a compressed state in the length direction.

The compressed state of the fabric layer in the length direction can take several different forms which can be present in elastic bandages of this invention.

In one form the fabric layer is wrinkled into lines of corrugation or ridges transverse to the width of the bandage. In another form only localised regions of the fabric are wrinkled for example the flexible strands between the rigid junctures of a net can be deformed by folding or twisting. In yet another form the fabric layer is compressed from its open form to a closed form, for example a net with diamond shaped apertures in open state can be compressed into a net with slit apertures and vice versa. The compressed state of the fabric in the length direction often results from the preferred methods of making the elastic bandages of the invention as hereinafter described. Alternatively the fabric can be in a compressed state before it is bonded to the elastomeric film layer. Suitable fabrics of this type include creped or crimped fabrics for example micro creped paper.

An elastic bandage of this construction has the advantage that fabric provides the bandage in a stretch state with a stop which limits the amount by which the bandage can be stretched and thus provides the bandage with a maximum bandaging stress. Thus, by the proper selection of materials and the degree of compression in the longitudinal direction of the fabric it is possible to make an elastic bandage which has the desired stress/strain characteristics including if necessary limits to the bandaging stress and the recoverable elastic strain.

It has now been found that an initial bandaging stress of approximately 90 g to 270 g/cm width (0.5 to 1.5 lb per inch width) more suitably 140 g to 230 g/cm width (0.8 to 1.3 lb per inch width) and preferably 180 g/cm width (1 lb per inch width) is desirable especially for the treatment of venous insufficiency of the leg. It is also desirable that the bandage should have sufficient recoverable strain at that stress to cope with the shrinkage of the bandaged area during treatment, for example the reduction of swelling during treatment of venous insufficiency of the leg.

It is desirable that the bandage should have a recoverable elastic strain in the length direction of at least 25% more suitable at least 50% desirably at least 75% and preferably at least 100% at a stress of 180 g/cm width (1 lb per inch width). Generally a recoverable elastic strain of more than 150% at a stress of 180 g/cm width (1 lb per inch width) is not required.

It is also desirable that the bandage should maintain a compressive stress on the area under the bandage, for example legs where in time the combination of a reduction in swelling and stress decay can understandably reduce the compressive stress of the bandage.

The elastomeric film present in the bandage of this invention provides the bandage with its desirable elastic properties. The elastomeric film can be continuous, macroporous or microporous. However, it is preferred that the elastomeric film in the bandage of this invention is continuous as this can produce a bacterial barrier which is desirable if infected areas are to be covered.

Therefore in another aspect the present invention provides a moisture vapour transmitting elastic bandage which comprises an inner layer of fabric and an outer layer of fabric bonded to a central layer characterised in that the central layer comprises a continuous elastomeric film.

Suitable films which may be obtained in continuous form and which transmit moisture vapour can be made from polyurethane, for example a thermoplastic polyurethane.

Certain preferred films are those made from the so-called 'Estanes' (Registered Trade Mark) of B. F. Goodrich Co. Ltd. Estanes are a range of thermoplastic polyester and polyether urethanes. A particularly apt film forming material is Estane 5714 which is a polyether urethane. Estane 5714 is described in 'Properties and Processing of Estane Polyurethane Materials' published by B. F. Goodrich August 1968.

The thickness and weight of the film used in the bandage of this invention can vary according to elastic and moisture vapour transmission properties required in the final bandage.

Suitable film thicknesses will generally be in the range $12.5\mu$ to $75\mu$ (0.005 to 0.003 inch) and more aptly $20\mu$ to $50\mu$ (0.0008 inch to 0.002 inch). Films of Estane 5714 have been found to be particularly suitable when $25\mu$ (0.001 inch) thick at which thickness the film has a moisture vapour transmission rate of $1800/m^2/22$ hours at 37° C. at 100%-10% relative humidity difference.

Optionally additives such as fillers, antioxidants or the like may be mixed into the film material before it is formed into a film. The addition of a filler such as silica (for example 5% Gasil (Trade Mark)) may be advantageous.

The suitable polyurethane films can be formed by casting from solution or by hot melt coating or extrusion in conventional manner.

The elastomeric film of the elastic bandages of the invention can have apertures. Elastic bandages with a central layer of apertured film will have high moisture vapour transmission rates. The bandages may also have increased capacity to absorb wound exudate if the excess exudate from an inner absorbent layer in contact with the wound can pass through the film apertures to an outer absorbent layer.

Therefore in a further aspect the present invention provides a moisture vapour transmitting elastic bandage which comprises an inner layer of fabric and an outer layer of fabric bonded to a central layer characterised in that the central layer comprises an apertured elastomeric film.

The number and size of the aperture in the apertured film may be sufficient to allow wound exudate to pass the film to an outer absorbent layer. Suitable apertured elastomeric films have apertures with a dimension of from 0.05 mm to 2.5 mm more preferably from 0.1 mm to 1 mm. Suitable apertured films have a thickness of 0.025 mm to 2.5 mm and preferably 0.05 mm to 0.15 mm. The apertured elastomeric film can be in any convenient form such as a perforated film or net.

In a favoured aspect of the invention the apertured elastomeric film is an integral net. The term 'integral net' means a net in which the strands and junctures are formed integrally during manufacture.

The elastomeric integral net of the elastic bandage of the invention can have any convenient form depending on the chosen arrangement of strand, juncture and hole areas and also their shapes and relative size.

In a preferred form the net consists of essentially of longitudinal and transverse strands to give a square grid hole pattern. Suitable nets of this type aptly have 4 to 40 apertures per cm and preferably 8 to 24 apertures per cm in both longitudinal and transverse directions.

Square grid pattern elastomeric integral nets of the elastic bandages of the invention may have transverse strands which are thicker than the longitudinal strands to provide a better resistance to 'necking' when the bandage is stretched in the longitudinal direction.

Normally the apertured elastomeric films are made of pharmaceutically acceptable water insoluble elastomer. Suitable elastomers include thermoplastic polymers of polyurethane, polybutadiene and butadiene-styrene block copolymers.

Preferred grades of thermoplastic polyurethanes are Estane polyurethanes as described hereinbefore in relation to continuous films.

A suitable polyurethane net is disclosed in U.S. Pat. No. 3,913,510.

The non-woven fabric used in a fabric layer of the bandages of this invention will generally have a weight of from 10 gsm to 80 gsm and more aptly from 12 gsm to 60 gsm, for example 18 gsm to 45 gsm.

The non-woven fabric employed may aptly have absorbent properties.

Suitable non-woven fabrics include those made from cellulosic fibres such as viscose rayon fibres, or other flexible material.

Preferred non-woven fabrics for use include apertured non-woven fabrics such as those made from bonded viscose filaments. A suitable fabric of this kind is available as Bemliese (Trade Mark) from Asahai Chemical Industry Co. Bemliese is available in weights ranging from 18-45 gsm which are particularly suitable for use in this invention. The Bemliese fabric has diamond shaped apertures arranged in staggered rows in the longitudinal direction. The fabric can be stretched in the transverse direction due to the ability of the aperture to change its shape from an open diamond to a slit in the transverse direction. A non-woven fabric of this structure has some ability to accommodate the change in dimensions of the fabric, depending on the degree of compression, when the non-woven fabric is in a compressed state.

The use of this or similar net-like non-woven fabric can provide a bandage which has a recoverable elastic strain in both longitudinal and transverse directions and has a surface appearance which is flat.

The integral thermoplastic nets should be sufficiently flexible to enable the net to be in a compressed state in the length direction when the bandage is in the unstretched condition.

The layer of integral thermoplastic net provides reinforcement for and modifies the elastic properties of the elastomeric film layer to give the desirable properties of the elastic bandages of the invention.

Suitable nets include nets made by biaxial stretching thermoplastic sheets embossed with a pattern of on one or both sides raised bosses, discrete cavities, parallel ribs and grooves or mixtures thereof. Process of making these nets are described in British Patent Specification Nos. 914,489, 1,055,963, 1,075,487, 1,110,051, 1,496,786 and 1,531,715.

A preferred integral thermoplastic net has sufficient rigidity in the transverse direction to resist the tendency of the elastic bandage to 'neck in' when stretched in a longitudinal direction.

A particularly apt integral thermoplastic net is a net ref. Y218 available from Smith & Nephew Plastics Ltd., Hull, U.K. The Y218 net is made by longitudinally stretching a high density polyethylene sheet embossed with a pattern of raised hexagon shapped bosses in a staggered arrangement. Y218 net has rows of approximately 10 per cm packed bosses in the transverse direction and approximately 4 per cm bosses in the length direction connected by flexible oriented strands. British Patent Specification No. 1,055,963 discloses suitable methods of making such nets.

The elastic bandage of this invention may be non-adhesive, self-adhesive or coated with a moisture vapour transmitting pressure sensitive adhesive. An adhesive elastic bandage can have a peelable protector, for example a silicone release coated paper, on an adhesive surface to enable a bandage in roll form to be easily unrolled.

The pressure sensitive adhesive coating (in adhesive bandages of this invention) can be in any convenient form. The adhesive may be discontinuous. Alternatively, the adhesive may be continuous.

The adhesive can be present on one or both of the outer surfaces of adhesive bandage of the invention.

Normally and preferably the pressure sensitive adhesive is continuous. Most aptly the adhesive has a moisture vapour transmission rate of at least 250 g and preferably at least 500 g/m$^2$/24 hrs at 37° C. at 100%-10% relative humidity difference. Suitable pressure sensitive adhesives which transmit moisture vapour as a continuous coat include various acrylate ester copolymers, polyvinyl ethyl ether and polyurethane adhesive. Examples of suitable adhesives are given in U.K. Specification No. 1,280,631. The pressure sensitive adhesives can be polymers per se, blends of polymers, mixtures of polymers with tackifying resins optionally other materials such as fillers and antioxidants.

A preferred pressure sensitive adhesive comprises a blend of high and low viscosity polyvinyl ethyl ethers in particular 'adhesive composition A' disclosed in British Patent Specification No. 1,280,631. Other preferred pressure sensitive adhesives comprise copolymers of acrylate ester with acrylic acid for example as disclosed in British Patent Application No. 2070631 and in particular a copolymer of 47 parts by weight of n-butylacrylate, 47 parts by weight of ethylhexyl acrylate and 6 parts by weight of acrylic acid polymerised in acetone according to the general method given in U.S. Pat. No. 2,884,126 and with an intrinsic viscosity of at least 1.9 dl/g.

The weight range of the adhesive coating is generally from 15 to 70 gsm and preferably from 20 to 45 gsm. The adhesive coating can be formed by any convenient method including solution and emulsion coating, coating from a hot melt and by extrusion.

It has been found that certain non-adhesive elastic bandages of the invention as hereafter described become adhesive when stretched longitudinally.

In yet a further aspect the invention provides a moisture vapour transmitting elastic bandage which comprises an inner layer of fabric and an outer layer of a fabric bonded to a central layer characterised in that the bandage becomes adhesive when stretched in a longitudinal direction by exposure of the adhesive used to bond a fabric layer to to the central film layer.

A favoured elastic bandage of this type comprises an integral thermoplastic net, typically net reference Y218 from Smith and Nephew Plastics Limited, bonded to a central layer of elastomeric film by a pressure sensitive adhesive. The non-adhesive bandage becomes adhesive when stretched due to the exposure of the pressure sensitive adhesive through the apertures of the net. A preferred elastic bandage has a layer of net bonded to both sides of the central layer of elastomeric film by a pressure sensitive adhesive.

In another aspect the invention provides a method of making an elastic bandage by bonding two layers of fabric to a central layer of elastomeric film in a stretched condition and thereafter allowing the composite to contract.

The elastic bandage of the invention using a net layer or layers can be made by two alternative processes. Both processes involve stretching the elastomeric film in a longitudinal direction. In one process the net layer is bonded to the elastomeric layer before stretching. In the second process the net layer is bonded to the elastomeric layer after stretching. A combination of these two processes is also possible.

In another aspect the invention provides a method of making a moisture vapour transmitting elastic bandage by bonding a layer of integral thermoplastic net to an elastomeric film in a stretched condition and thereafter allowing the composite to contract.

In another aspect the invention provides a method of making moisture vapour transmitting elastic bandages which comprises bonding a layer of integral thermoplastic net or net precursor material to an elastomeric film stretching the laminate in a longitudinal direction and allowing the laminate to contract.

A net precursor material is a material which will form an integral thermoplastic net when stretched in a longitudinal direction.

Preferred net precursor materials are embossed thermoplastic sheets described hereinbefore which have been given a stretch in the transverse direction.

Preferred net precursor materials are disclosed in British Patent Specification No. 1531715. Suitably apt net precursor materials are described in Examples 1 and 2 of British Patent Specification No. 1531715. These net precursor materials can be given a longitudinal stretch in the region of 100% to 200% to form open nets. A longitudinal stretch in the region of 10% to 50% will give partially opened nets or net precursor material which are also suitable for the process of this invention.

It is desirable that the precursor net material can be stretched at least 50%, more suitable 75% and preferably at least 100% in the longitudinal direction before breaking.

The bonding may be effected in any convenient manner such as by heat sealing or the use of an adhesive such as a solvent adhesive.

It is preferred that the fabric layers are bonded to the elastomeric film by means of an adhesive. Suitable adhesives for use include hot melt adhesives, solvent adhesives, pressure sensitive adhesives, and contact adhesives.

The adhesive coating or layer can transmit moisture vapour. Suitable moisture vapour transmitting pressure sensitive adhesives are those described hereinbefore for the adhesive coating on the external surface of the adhesive form of the bandage.

The pressure sensitive adhesive employed at a weight of from 5-50 gsm and preferably from 10-30 gsm.

In the process of making the bandage it is desirable that the elastomeric film is stretched in a longitudinal direction.

It is preferred that the elastomeric film is longitudinally stretched under biaxial stress conditions to limit the amount by which the film contracts in the transverse direction, for example by longitudinally stretching the film over rollers. Elastic bandages made by this process when stretched longitudinally will contract less in the transverse direction (that is 'neck' less) than elastic bandages made by a process where the elastomeric film is stretched in 'free flight' without lateral restraint. The amount of stretch will depend on the recoverable elastic strain required in the bandage.

It is desirable that the film should be stretched by at least 75% and preferably by at least 100% during manufacture.

If two layers of non-woven fabric are used to form the elastic bandage of the invention it is preferred that the two layers are bonded to the stretched film in the same operation.

Figure 2:
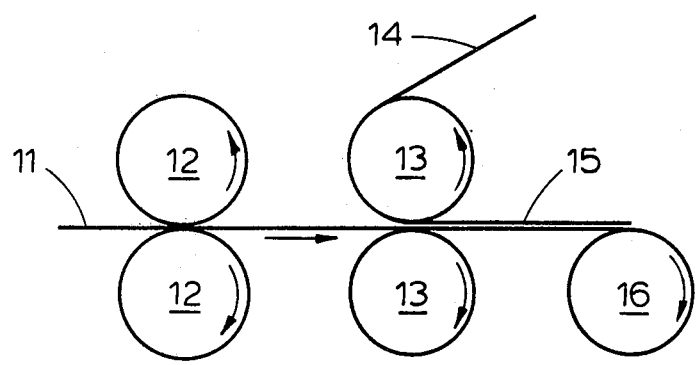
Figure 3:
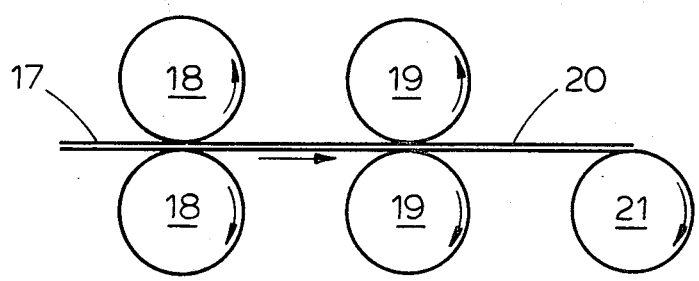

FIGS. 1, 2 and 3 illustrate processes for manufacturing bandages of the invention.

In FIG. 1 a laminate 1 of an elastomeric film coated on both sides with a pressure sensitive adhesive and protected on both sides with a release paper is fed in pressure contact between the nip of two rotating rollers 2 and the release paper 3 and 4 removed. The adhesive coated elastomeric film 5 is passed under pressure through the nip of rollers 6 which are rotating at a surface speed faster than rollers 4 so that film 5 is in a stretched condition. The film 5 is bonded to non-woven fabrics 7 and 8 which are fed simultaneously into the nip. The resulting laminate 9 is then wound onto roller 10, which is rotating at a surface speed similar to that of rollers 2. The bandage sheet 9 thus contracts under low tension. The bandage sheet is thereafter cut into individual bandages.

FIG. 2 illustrates an alternative process for making a bandage of the invention in which the pressure sensitive adhesive is pre-coated onto one side of each of the non-woven fabric layers instead of on both sides of the elastomeric film. This process has the advantage that the surfaces of the elastomeric film are non-tacky during the stretching stage thus preventing the film sticking to the rollers.

In FIG. 2 elastomeric film 11 is passed between the nip of rollers 12 and then between the nip rollers 13 rotating at a surface speed faster than that of rollers 12 where the elastomeric film is stretched longitudinally and laminated to pressure sensitive adhesive coated thermoplastic net 14 fed into the nip of rollers 13. The resultant laminate sheet is wound onto roller 16 rotating at a surface speed similar to that of rollers 12. The sheet 15 is thus allowed to contract under low tension.

Another layer of adhesive coated fabric is then laminated to the other side of the elastomeric film laminate by the same process. Alternatively, another layer of adhesive coated fabric can be laminated to the other side of the elastomeric film simultaneously with net layer 14 by passage through nip rollers 13. The bandage sheet is thereafter cut into individual bandages.

In FIG. 3 a bonded laminate 17 of net precursor material and the elastomeric film is fed between nip rollers 18 and is then stretched longitudinally by passage through nip rollers 19 rotating at a surface speed faster than that of rollers 18 to form a sheet 20 of a net bonded to an elastomeric film. Sheet 20 is then wound onto roller 21 which is rotating at a surface speed similar to that of rollers 18 so that the sheet 20 is allowed to contract under low tension.

A second net precursor layer is then laminated to the elastomeric film side of sheet 20 and the laminate subjected to a second stretching and contracting process to form a bandage sheet. The bandage sheet is thereafter cut into individual bandages.

In an alternative and preferred process of making the bandage sheet, sheet 17 can be a bonded laminate of an elastomeric film between an inner and outer layer of net precursor material. This process enables the bandage sheet to be formed in a single stretching and contracting process.

In a second alternative process of forming the bandage sheet an adhesive coated non-woven fabric is laminated to the elastomeric film side of sheet 17 by passage between the nip of rollers 19 in similar manner to that illustrated in FIG. 2.

EXAMPLE 1

A 10 cm×10 cm×0.025 mm thick film of Estane 5714 containing 5% Gasil filler was coated on both sides by a knife over flat bed coating unit with 33% solids solution in acetone of an acrylate ester copolymer adhesive and dried in an oven at 80° C. to give a dry coating weight on both sides of the film of 12 gsm. The adhesive was a copolymer of 47 parts by weight n-butyl acrylate, 47 parts by weight of ethylhexyl acrylate, 6 parts by weight of acrylic acid having an intrinsic viscosity of 1.9. The coated film was stretched by 100% to give a film 20 cm long×7 cm wide and an 18 gsm apertured Bemliese non-woven fabric bonded to both sides under pressure. The stretched laminate was allowed to contract free of tension to a bandage speed 10.5 cm long×9.3 cm wide.

The bandage of the Example had the following properties:

(i) Moisture vapour transmission rate: 1600 g/m$^2$/24 hrs at 37° C. at 100%-10% RH difference.
(ii) Strain at 180 g/cm width (1 lb per inch width) stress: 80%
(iii) Weight: 140 gsm.

The bandage of this Example also had a recoverable elastic strain in the transverse direction. The non-woven fabric surfaces of the bandage were in a flat compressed state. A surprising feature of the bandage was that a 180 g/cm stress can be obtained with 100% strain in longitudinal direction whereas the same stress in a 25μ (0.001 inch) Estane 5714 film requires a strain of not less than 500%.

EXAMPLE 2

A 10 cm×10 cm×0.025 mm thick film of Estane 5714 containing 5% Gasil filler was coated on both sides by a knife over flat bed coating unit with 33% solids solution in acetone of an acrylate ester copolymer adhesive and dried in an oven at 80° C. to give a dry coating weight on both sides of the film of 12 gsm. The adhesive was a copolymer of 47 parts by weight of n-butyl acrylate, 47 parts by weight of ethyl hexyl acrylate and 6 parts by weight of acrylic acid having an intrinsic viscosity of 1.9. The coated film was stretched by 100% to give a film 20 cm long by 7 cm wide and an 18 gsm apertured Bemliese non-woven fabric bonded to one side and a net ref. Y218 from Smith and Nephew Plastics Limited bonded to the other side under pressure. The stretched laminate was allowed to contract free of tension to form the product.

The resulting bandage did not 'neck in' at a 72% strain and had 72% strain at 180 g/cm inch width (1 lb per inch) stress.

The bandage of this example did not possess significant adhesive properties in the unstretched form but when stretched exhibited adhesive properties.

EXAMPLE 3

A 10 cm×10 cm coated Estane 5714 film was prepared as Example 1. A net precursor material of Example 1 of British Patent Specification No. 1531715 was bonded to both sides of the coated film. The laminate was stretched by 135% to give a length of 23.5 cm and the stretched laminate allowed to contract free of tension to form the product.

The bandage did not 'neck in' at 70% strain and had 70% strain at a stress of 180 g/cm inch width (1 lb per inch).

EXAMPLE 4

A 10 cm×10 cm coated Estane 5714 film was prepared as Example 1. A net precursor material of Example 1 of British Patent Specification No. 1531715 was laminated under pressure to one side of the coated film. The laminate was stretched by 100% to give a length of 20 cm and an 18 gsm Bemliese non-woven fabric laminated to the exposed adhesive side of the stretched laminate. The stretched laminate was allowed to contract free of tension to form the product.

The resulting bandage did not 'neck in' at a 42% strain and had a 42% strain at a 180 g/cm inch width (1 lb per inch) stress.

EXAMPLE 5

An adhesive elastic bandage was made by laminating under pressure, by passage through nip rollers, the bandage sheet of Example 1 and a silicone coated release paper (Steralease 67 available from Sterling Coated Papers Limited) coated with the acrylic copolymer adhesive (30 gsm) of Example 1. The bandage sheet laminate was wound into a roll with the siilicone coated release paper acting as a protector for the adhesive coating to form an adhesive elastic bandage. The silicone paper protector can be removed before or during the application of the adhesive bandage to the patient.

What we claim is:

1. A moisture vapour transmitting elastic bandage which comprises an inner layer of fabric and an outer layer of fabric bonded to a central layer, said central layer comprising an apertured elastomeric film which allows the passage of wound exudate from the inner layer to the outer layer and whereby the bandage has a recoverable elastic strain in the length direction of 25% to 150% at a stress of 180 g/cm.

2. An elastic bandage as claimed in claim 1 in which a fabric layer is in a compressed state in the length direction.

3. An elastic bandage as claimed in claim 1 in which the central layer comprises a polyurethane.

4. An elastic bandage as claimed in claim 1 in which a fabric layer comprises an absorbent non-woven fabric.

5. An elastic bandage as claimed in claim 1 in which a fabric layer comprises an integral thermoplastic net.

6. A method of making an elastic bandage of claim 1 which comprises bonding an inner layer of fabric and an outer layer of fabric to a central layer of apertured elastomeric film in a stretched condition and thereafter allowing the composite to contract.

7. A method of making an elastic bandage of claim 5 which comprises bonding a layer of integral thermoplastic net or net precursor material to an apertured elastomeric film, stretching the laminate in a longitudinal direction and thereafter allowing the laminate to contract.

8. An elastic bandage according to claim 1 in which the apertured film is an integral net.

9. A moisture vapour transmitting elastic bandage which comprises an inner layer of fabric and an outer layer of fabric bonded by an adhesive to a central apertured film layer, said bandage becoming adhesive when stretched in a longitudinal direction by exposure of the adhesive through the apertures.

10. An elastic bandage according to claim 1 in which the apertured elastomeric film has 8 to 24 apertures per cm with a dimension of 0.1 to 1 mm.

11. An elastic bandage according to claim 8 in which the integral net has longitudinal and transverse strands.

12. An elastic bandage according to claim 1 in which the bandage has an initial bandaging stress of 140 g/cm to 230 g/cm.

* * * * *